(12) United States Patent
Rao

(10) Patent No.: US 7,457,731 B2
(45) Date of Patent: Nov. 25, 2008

(54) EARLY DETECTION OF DISEASE OUTBREAK USING ELECTRONIC PATIENT DATA TO REDUCE PUBLIC HEALTH THREAT FROM BIO-TERRORISM

(75) Inventor: R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 741 days.

(21) Appl. No.: 10/319,365

(22) Filed: Dec. 13, 2002

(65) Prior Publication Data

US 2003/0177038 A1 Sep. 18, 2003

Related U.S. Application Data

(60) Provisional application No. 60/340,634, filed on Dec. 14, 2001.

(51) Int. Cl.
*G06F 17/10* (2006.01)
(52) U.S. Cl. .............. 703/2; 705/7; 705/2; 705/3; 600/300; 707/100; 707/104.1; 707/9
(58) Field of Classification Search .......... 600/300, 600/407; 705/2, 7; 707/104.1, 100; 704/270; 715/530
See application file for complete search history.

(56) References Cited

U.S. PATENT DOCUMENTS

| | | | | |
|---|---|---|---|---|
| 5,664,109 | A * | 9/1997 | Johnson et al. | 705/2 |
| 6,059,724 | A * | 5/2000 | Campell et al. | 600/300 |
| 6,108,635 | A * | 8/2000 | Herren et al. | 705/2 |
| 6,173,068 | B1 * | 1/2001 | Prokoski | 382/115 |
| 6,278,999 | B1 * | 8/2001 | Knapp | 707/9 |
| 6,766,277 | B2 * | 7/2004 | Siegel | 702/187 |
| 2001/0041991 | A1 * | 11/2001 | Segal et al. | 705/3 |
| 2002/0068857 | A1 * | 6/2002 | Iliff | 600/300 |
| 2002/0082886 | A1 * | 6/2002 | Manganaris et al. | 705/7 |
| 2002/0087274 | A1 * | 7/2002 | Alexander et al. | 702/19 |
| 2002/0133502 | A1 * | 9/2002 | Rosenthal et al. | 707/104.1 |
| 2002/0138524 | A1 * | 9/2002 | Ingle et al. | 707/530 |
| 2002/0178031 | A1 * | 11/2002 | Sorensen et al. | 705/2 |
| 2002/0183965 | A1 * | 12/2002 | Gogolak | 702/179 |
| 2002/0188452 | A1 * | 12/2002 | Howes | 704/270 |

(Continued)

OTHER PUBLICATIONS

"Installation Force Protection Guide" United States Air Force 1997.*

(Continued)

*Primary Examiner*—Kamini Shah
*Assistant Examiner*—Cuong V Luu
(74) *Attorney, Agent, or Firm*—Donald B. Paschburg

(57) ABSTRACT

A method is provided for automatically identifying a disease outbreak indicative of a potential bio-terror attack. Patient records are mined from structured and unstructured clinical sources. The patient records are then analyzed by correlating selected patient data contained in the patient records with disease indicia for each of a plurality of diseases. A probability of a disease outbreak is estimated at least in part based on these correlations. Suspicion may also be indicated if anomalous disease clusters are found. If any of the estimated probabilities exceeds a threshold value, a disease outbreak alert is outputted. The disease indicia may be defined by disease progression models, which may be stored in a disease knowledge base.

53 Claims, 4 Drawing Sheets

U.S. PATENT DOCUMENTS

| | | | |
|---|---|---|---|
| 2003/0013951 A1* | 1/2003 | Stefanescu et al. | 600/407 |
| 2003/0036684 A1* | 2/2003 | Hood et al. | 600/300 |
| 2003/0046305 A1* | 3/2003 | Clarkson | 707/104.1 |
| 2003/0065669 A1* | 4/2003 | Kahn et al. | 707/100 |
| 2003/0074564 A1* | 4/2003 | Peterson | 713/182 |
| 2003/0144884 A1* | 7/2003 | Mayaud | 705/3 |
| 2005/0015276 A1* | 1/2005 | Sullivan et al. | 705/2 |

OTHER PUBLICATIONS

Hutwagner, L.C. et al. "Using Laboratory-Based Surveillance Data for Prevention: An Algorighm for Detecting Salmonella Outbreaks." Emerging Infectious Diseases, vol. 3 No. 3. Jul.-Sep. 1997.*

Young, Donna. "Leaders, a Medical Surveillance System, Gives Health Officials a Powerful New Weapon in the Fight Against Infectious Diseases." GCN First Alert, May 2001.*

"Biological and Chemical Terrorism: Strategic Plan for Preparedness and Response." US Department of Health and Human Services, Apr. 21, 2000.*

"The use of Technology in Preparing Subway Systems fro Chemical/Biological Terrorism," Policastro et al, Sandia National Laboratory, Apr. 1999.*

Dato V, Wagner M, Allswede M, Aryel R, Fapohunda A. The nation's current capacity for the early detection of public health threats including bioterrorism. Washington, DC: Agency for Healthcare Research and Quality, 2001.*

Robin Hanson, John Stutz, and Peter Cheeseman. Bayesian Classificaiton Theory Research Institute for Advanced Computer Science, 1991.*

Othar Hansson, Andrew Mayer Probabilistic Heyristic Estimates Annals of Mathematics and Artificial Intelligence, 2, 1990, pp. 209-220.*

Bruce D'Ambrosio Inference in Bayesian Networks American Association for Artificial Intelligence, 0738-4602-1999, Summer 1999.*

Brian Bennet U.S. Biodefense and Homeland Security: toward Detection and Attribution Naval Postgraduate School, Dec. 2006.*

Chemical and Biological Arms Control Institute Bioterrorism in the United States: Thread, preparedness, and Response Contract No. 200*1999*00132, Nov. 2000.*

U.S. Patent Application entitled "Patient Data Mining" based on U.S. Appl. No. 60/335,542, inventors: R. Bharat Rao, Ph.D. et al., pp. 1-40.

* cited by examiner

EARLY DETECTION OF DISEASE OUTBREAK USING ELECTRONIC PATIENT DATA TO REDUCE PUBLIC HEALTH THREAT FROM BIO-TERRORISM

CROSS REFERENCE TO RELATED APPLICATIONS

This application claims the benefit of U.S. Provisional Application Ser. No. 60/340,634 filed on Dec. 14, 2001, which is incorporated by reference herein in its entirety.

FIELD OF THE INVENTION

The present invention relates to medical information processing systems, and, more particularly to a computerized method and system for automated identification of disease outbreak to reduce the threat from bio-terrorism.

BACKGROUND OF THE INVENTION

To reduce the public health threat from bio-terrorism, various government agencies, including the Centers for Disease Control and Prevention (CDC), have issued guidelines for health care professionals about recognizing illnesses that might be associated with intentional release of biologic agents. Although these guidelines are helpful, many diseases with recognized bio-terrorism potential (e.g., smallpox) mimic relatively common illnesses such as influenza, and can be difficult to detect at an early stage even with increased knowledge and awareness.

Another approach is to require doctors to fill out "disease templates" when the physician treats "suspicious" patients. However, this does not satisfy the need for early detection, as subtle patterns can escape detection by the physician unless seen in a larger context. Moreover, individual physicians and hospitals may not be able to rapidly detect unusual clusters of acute illness. A cluster of related symptoms in a small geographic region could signal an early outbreak. However, each case individually might look relatively benign.

Furthermore, the concept of filling out a "suspicious patient template" is fundamentally flawed. If the doctor has suspicion about a patient, then there are a many other ways to confirm that the patient is the victim of bio-terrorism. It is the patient who does not raise a red flag until it is too late that we are most concerned about.

It is worth reflecting that for at least two of the anthrax patients who died, part of the problem was an initial misdiagnosis. For a virulent disease such as smallpox, which may be even harder to diagnose, detecting the disease a day or two earlier (some studies have suggested that even hours may make a big difference) might prevent or at least control its spread.

Attempts have been made to analyze available hospital admissions information to rapidly detect an attack. For example, an artificial intelligence system called the Real-time Outbreak Detection System (RODS), developed jointly by the University of Pittsburgh and Carnegie-Mellon University, examines hospital admissions records for hidden patterns. Although RODS is promising in some respects, results are hampered by the use of admissions information. Better results could be obtained if the entire patient record was consulted. For instance, during the recent anthrax attacks, no spike in admissions of an unusual nature took place, and only clinical information could have revealed an outbreak of anthrax.

Currently, clinical information is stored in a myriad of structured and unstructured data sources. It may be necessary to access numerous different databases, each with its own peculiar format. Worse, physician notes may have to be consulted. These notes usually are nothing more than free text dictations, and it may be very difficult to sift through the notes to gather the necessary information. Yet only unstructured data may reveal important indications of an unusual disease outbreak. (At least if we hope to detect it before there are sufficient cases that lead to an increase in admissions).

Given the importance of early detection of unusual disease incidents, it would be desirable and highly advantageous to provide new techniques for automatically identifying disease outbreak to reduce the threat from bio-terrorism.

SUMMARY OF THE INVENTION

The present invention provides techniques for automatically identifying a disease outbreak indicative of a potential bio-terror attack. This may be accomplished in two ways: (1) Identify patients that potentially match templates consistent with known bio-terrorism diseases (e.g., smallpox, anthrax, Ebola). Potentially, if the match is good enough, a single patient would be sufficient to raise an alert. Alternately, multiple patients partially matching a template may cause an alert. (2) Identify patient clusters with unusual disease patterns.

According to various exemplary embodiments of the present invention, patient records are obtained from structured and unstructured data sources. The patient records are then analyzed by correlating selected patient data contained in the patient records with disease indicia for each of a plurality of diseases. A probability of a disease outbreak is estimated at least in part based on these correlations. If any of the estimated probabilities exceeds a threshold value, a disease outbreak alert is outputted. The disease indicia may be defined by disease progression models, which may be stored in a disease knowledge base. For example, the smallpox model may include flu-like symptoms in the first 2-3 days, high fever, rash on the $4^{th}$-$7^{th}$ day.

As seen from the smallpox example above, at least some of the disease indicia may be temporally defined. Further, partial matches between the selected patient data and the disease indicia for a disease of interest may also trigger an alert. So, too might be the case where the specified disease indicia includes a cluster of patients having one or more symptoms. For example, an alert might be issued if ten patients in a particular geographic area all had flu-like symptoms, rash, and high fever that partially match the smallpox template.

Because it is important to maintain privacy, patient information associated with a disease outbreak alert should not include data regarding the identity of patients. Patient identification may be stripped off medical data before transmitting it to an outside facility. Alternately, all that could be shipped could be the results of findings, as in "Patient with rash on $4^{th}$ day of high fever: partial match to smallpox template." Then it would be up to the expert viewing the data to decide how to best proceed: request the entire patient record, contact the attending physician, request extra tests, quarantine, etc.

The data sources used to determine the disease outbreak will preferably include the entire patient record. This would entail the use of both structured data sources and unstructured data sources. The structured data sources may include various data bases, e.g., laboratory database, prescription database, test result database. The unstructured data sources may include information in text format (such as treatment notes, admission slips, and reports), image information, and waveform information. This would allow a patient to be tracked not just in the emergency room, but also through the intensive care unit, radiology, etc.

As mentioned, a disease outbreak alert may be issued when the estimated probability of a disease outbreak exceeds a threshold value. The threshold value may vary depending on disease, terror threat level, and be adjusted to reduce false alerts. In situations where the threat level for a particular disease is very high (based, for instance, on a government warning), the tolerance for false positives could be somewhat relaxed.

Advantageously, the method may be performed at either a health care facility or elsewhere. For example, the correlating step may be performed at a central location and the data sources may be provided using a networked hospital information system. The outputted disease outbreak alert can be sent to a monitoring facility or government agency. Local authorities may also receive this information to take appropriate action.

Finally, the present invention could be used for disease surveillance, to track naturally occurring diseases, for instance, the CDC's tracking of "selected notifiable diseases" published in the CDC Morbidity and Mortality Weekly Report (cdc.gov/mmwr/PDF/wk/mm6148.pdf). Occurrences of these diseases could be tracked both to test and calibrate the system (for bio-terrorism which would be the same, except with different disease templates), but also for disease surveillance.

These and other aspects, features and advantages of the present invention will become apparent from the following detailed description of preferred embodiments, which is to be read in connection with the accompanying drawings.

DESCRIPTION OF PREFERRED
EMBODIMENTS

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

It is also to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

Figure 1:
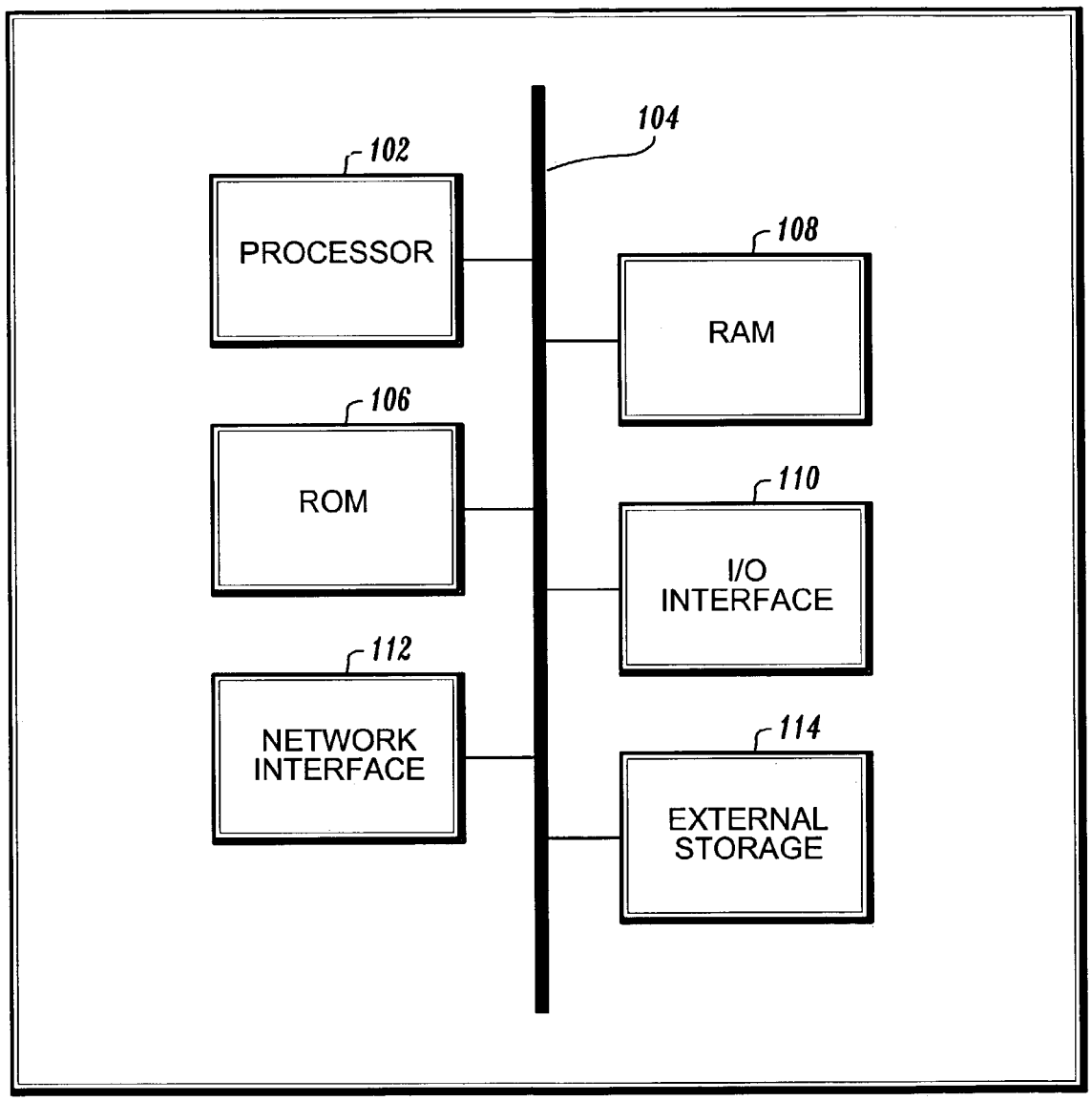
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
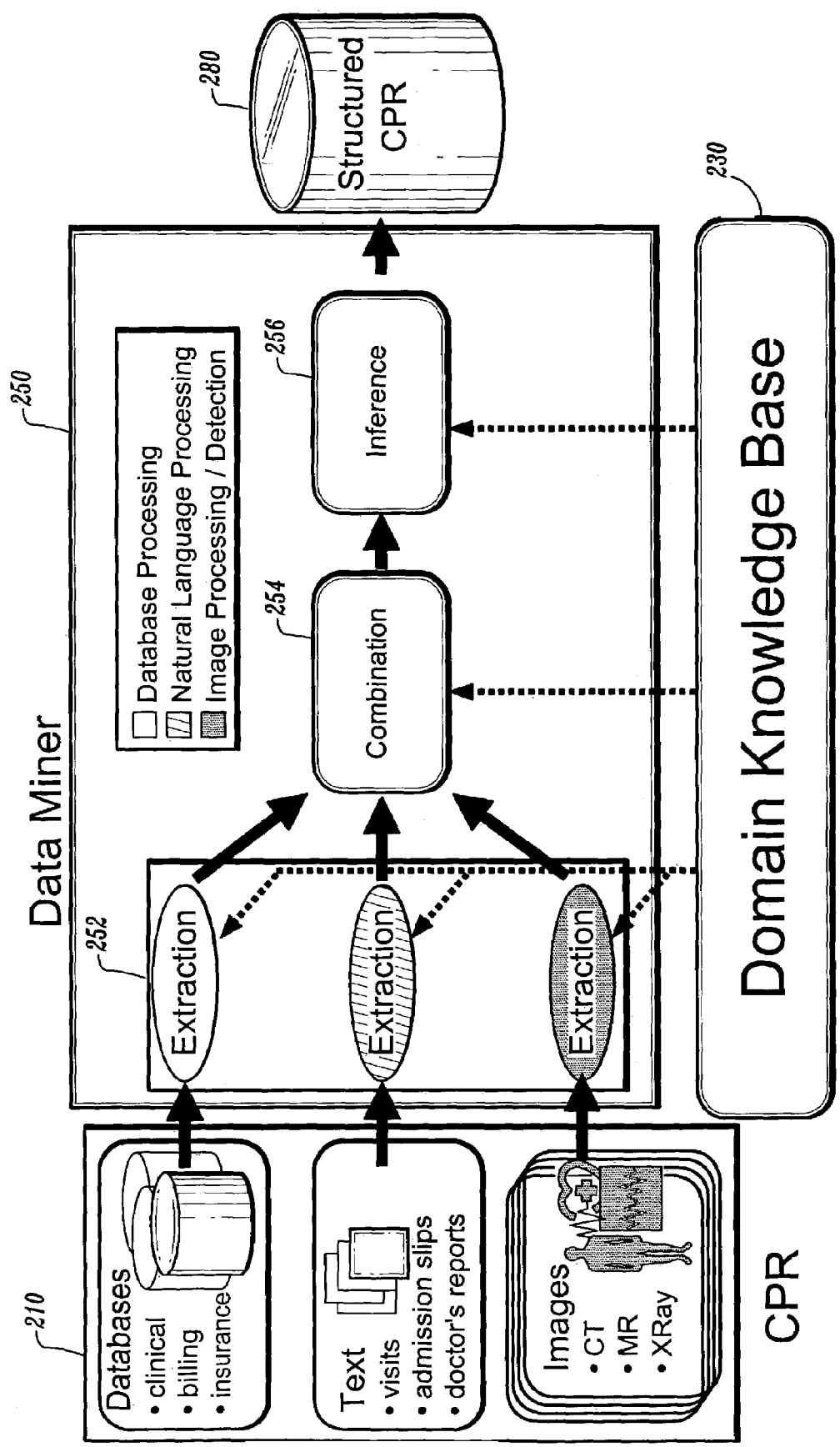
FIG. 2 shows an exemplary data mining framework for mining structured clinical information.

FIG. 2 illustrates an exemplary data mining framework as disclosed in "Patient Data Mining," by Rao et al., U.S. Patent Application Publication No. 2003/0120458, filed on Nov. 2, 2002, which is incorporated by reference herein in its entirety.

As illustrated in FIG. 2, an exemplary data mining framework for mining high-quality structured clinical information includes a data miner 250 that mines information from a computerized patient record (CPR) 210 using domain-specific knowledge contained in a knowledge base (230). The data miner 250 includes components for extracting information from the CPR 252, combining all available evidence in a principled fashion over time 254, and drawing inferences from this combination process 256. The mined information is stored in a structured CPR 280.

The extraction component 252 deals with gleaning small pieces of information from each data source regarding a patient, which are represented as probabilistic assertions about the patient at a particular time. These probabilistic assertions are called elements. The combination component 254 combines all the elements that refer to the same variable at the same time period to form one unified probabilistic assertion regarding that variable. These unified probabilistic assertions are called concepts. The inference component 156 deals with the combination of these concepts, at the same point in time and/or at different points in time, to produce a coherent and concise picture of the progression of the patient's state over time.

The present invention builds on the data mining framework depicted in FIG. 2. It makes use of the mined information stored in the structured CPR 280 to identify patients with indications of illness associated with the release of a biologic agent.

Figure 3:
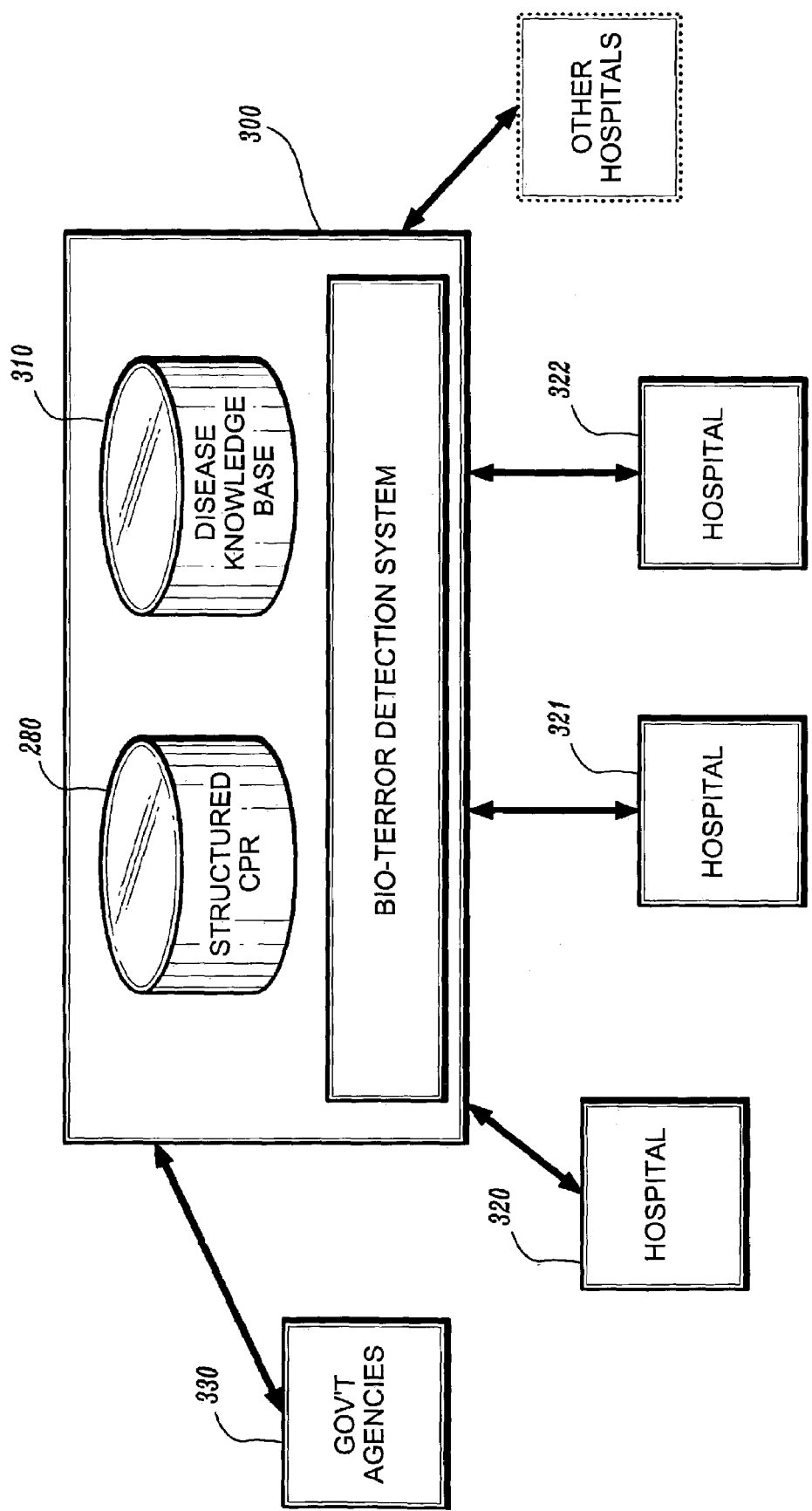
FIG. 3 shows an exemplary automated disease outbreak detection system.

Referring to FIG. 3, an automated bio-terror detection system 300 is illustrated. The automated bio-terror detection system 300 is operatively connected to the structured CPR 280 and includes a disease knowledge base 310. Hospitals 320-322 and government agencies 330 may communicate with the automated bio-terror detection system 300 via a suitable network (not shown). To comply with privacy requirements, patient identification may be stripped off medical data before transmitting it to an outside facility.

It must be emphasized that the data sources used to determine the disease outbreak will preferably include the entire patient record. This entails the use of both structured data sources and unstructured data sources. The structured data sources may include various data bases, e.g., laboratory database, prescription database, test result database. The unstructured data sources preferably will include information in text format (such as treatment notes, admission slips, and reports), image information, and waveform information.

In operation, the data miner 250 mines patient medical records for patients being treated at various health care facilities, such as the hospitals 320-322. The data miner 250 then forms concepts (probabilistic assertions about various aspects of the patient e.g., a progression of symptoms), and stores this information in the structured CPR 280. For example, from statements found in a medical treatment note, it may be concluded, with some degree of probability, that the patient has fever, flu-like symptoms, and a rash on face and forehead, with lesions. In addition, the disease progression of the illness may be determined.

The automated bio-terror detection system 300 retrieves patient clinical information from the structured CPR 280, and consults disease models stored in the disease knowledge base 310. For each disease, a template with various disease indicia are obtained, and correlated with the elemental information selected from the structured CPR 280. For example, the disease indicia for smallpox may include a 2-4 day period of fever before rash onset. Other indicia of smallpox are that the rash is most prominent on the face and extremities, with lesions developing at the same time. Patients having all of these symptoms will correlate highly; those with fewer similarities will correlate to a lesser degree. As will be discussed in greater detail with respect with FIG. 4, a disease outbreak may be indicated even when relatively low individual correlation values exist, if there is a cluster of patients each with similar disease indicia.

Figure 4:
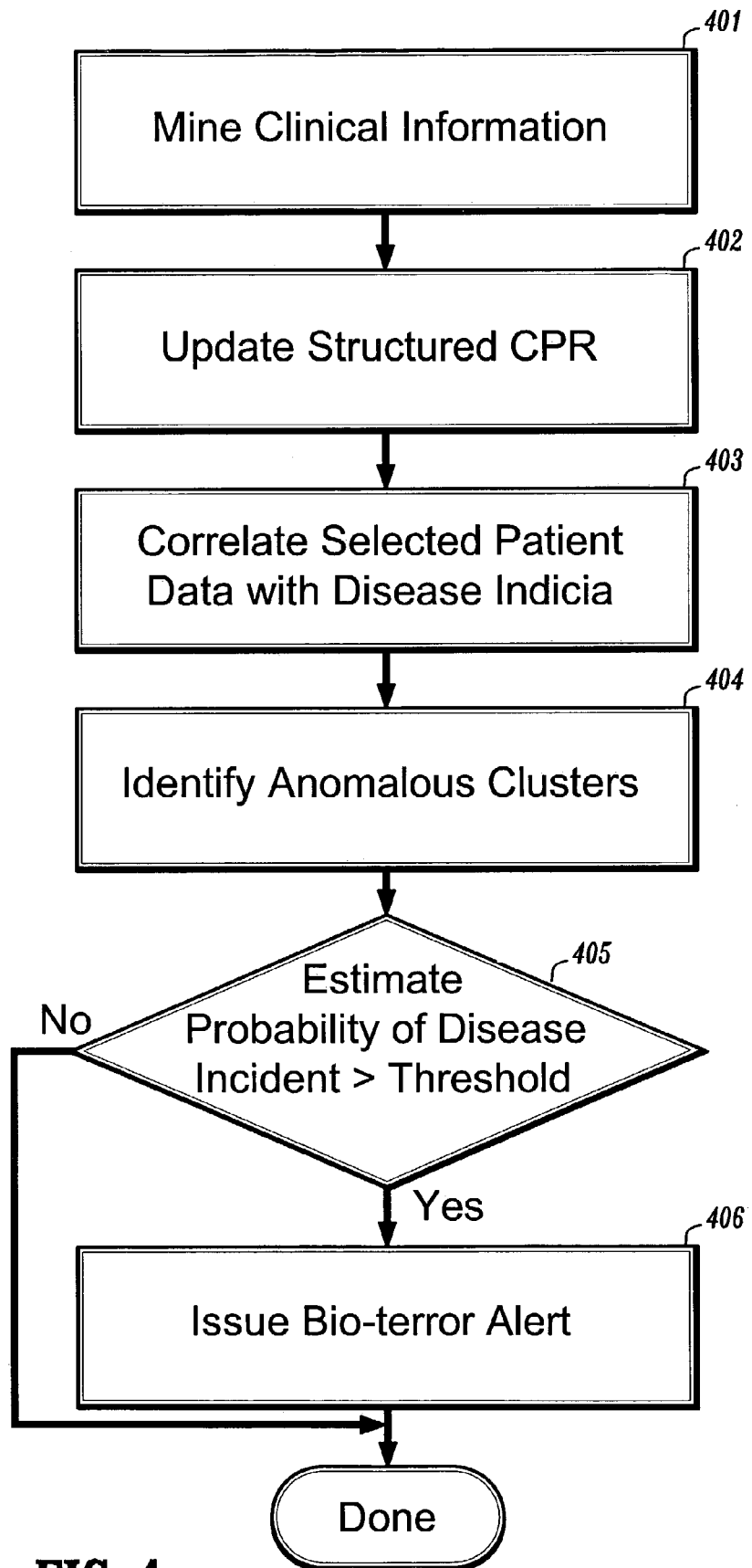
FIG. 4 shows a flow diagram outlining an exemplary technique for automatically identifying disease outbreak.

Referring now to FIG. 4, a flow diagram depicting an exemplary technique for identifying disease outbreak is illustrated. (It should be appreciated that the method shown in FIG. 4 can be used in conjunction with the system of FIG. 3).

In step 401, clinical information is mined from structured and unstructured data sources. Next, in step 402, a structured data source is updated with the mined patient information. As discussed, the data mining system described in "Patient Data Mining," by Rao et al., U.S. Patent Application Publication No. 2003/0120458, filed on Nov. 2, 2002, will preferably be used to perform these steps.

Next, in step 403, selected concepts obtained from the structured data source are correlated with disease indicia for each of a plurality of diseases. Disease indicia refers to the clinical features associated with a particular disease. A probability of a disease outbreak can be estimated at least in part based on these correlations. The disease indicia may be defined by disease progression models, which may be retrieved from a disease knowledge base.

For instance, the disease indicia for smallpox may include a fever during the first 2-4 days followed by a rash on the face, with lesions. The disease indicia for anthrax may include initial symptoms of one or more of fever, dyspnea, cough, and chest discomfort. Approximately 2-4 days after the initial symptoms, there may be a period of brief improvement followed by respiratory failure and hemodynamic collapse. The disease indicia for plague may include fever, cough with mucopurulent sputum, hemotysis, and chest pain. Furthermore, a chest radiograph will show evidence of bronchopneumonia.

Partial matches between the selected patient data and the disease indicia could also trigger suspicion. Additionally, where the specified disease indicia includes a cluster of patients having one or more symptoms, high level suspicion may be warranted. For example, suspicion might be raised if ten patients in a particular geographic area all have flu-like symptoms, rash, and lesions. Suspicion might also be raised if not all of the patient symptoms match expected symptoms for a particular disease. Although each case individually may be assigned a probability below the threshold, the joint probability for a group of patients might exceed the threshold, triggering an alert. In each of these cases, the criteria for determining the pertinent criteria can be obtained from expert knowledge, and the disease knowledge base can be designed to capture the expertise.

To understand how partial matching may be done, let us view a disease template as a combination of a series of token concepts. For instance early indications for disease X may be defined as concepts A, B, C, D, E where the concepts A, B, C, D, and E, may be high fever (e.g., >104 degrees), rash, vomiting, swelling, and back ache. There may be precise constraints such as, A (high fever) lasting at least 6 days, B (rash) occurring after the $4^{th}$ day, C (vomiting) intermittent in the early days of high fever, D (swelling) to follow C, and E (back ache) may occur at any time. (As can be seen, the constraints may be precise or simply ordering constraints).

An exact match will occur if all of the concepts are met, with the constraints satisfied for instance, a patient matches A, B, C, D, and E, with the temporal constraints as satisfied above. In this case a single patient may be enough to generate an alert.

A partial match may occur in two ways. First a patient only matches some of the concepts in the template—for example, a patient matches A, C, and D, but no information is present about B and E. Another way is that a patient may match a specific concept partially—for instance, instead of matching "A" (high fever for at least 6 days) completely, the patient may only have had fever for 4 days (only been admitted for 4 days). Either way, a score can be generated indicating how well a patient's record matches a particular disease template. Then an alert may only be issued if many patients partially match a disease template.

Here, the disease criteria have been matched with probability 1, i.e, there is a 100% probability that the early indications for disease have been met. (This does not mean that the patient has the disease; just that there is sufficient evidence to conclude that an alert needs to be raised).

For example, if 4 of the 5 concepts for a disease are met, a simple way to compute the probability of a partial match could be 4/5=80%. However, more sophisticated methods could take into account the significance of each of the concepts and the degree of match of the patient record with each concept in computing the probability of a match. If two patients match a disease X with probability p1 and p2 (and assume p1≧p2), the joint probability that at least one patient has Disease X, is at least p1 (or more likely greater). There are many ways to compute this probability; under a simpleminded assumption, this could be computed as 1−(1−p1)*(1−p2). Again, more sophisticated methods that take into account geographical proximity or other similarities between patients could be employed to compute the joint probability that at least one of the 2 patients has X. This can easily be extended to N patients.

Further, disease X above may also have concepts O, P, and Q as late indications of disease. In which case, a single patient partially matching the early stage concepts, but matching one or more of the late stage concepts may generate an alert (though ideally, the hope would be to raise an alert even before the patient matches any of the late stages).

In step 404, anomalous clusters are identified. In this case, suspicion may be raised if not all of the patient symptoms match expected disease indicia for a particular disease (disease template), but are viewed to be "anomalous"—i.e., they do not match any previously seen pattern in the historical patient data (that may stretch back several years). For instance, on noticing 50 patients were treated in hospitals in the San Francisco area all with symptoms including (possibly a subset of) moderate fever, swollen glands, rash on the lower back, lower back pain, and difficulty urinating—this may be an unusual combination (although not matching any of the disease templates) that could be worthy of examination by an expert. Although each case individually may be assigned a probability below the threshold, the joint probability for a group of patients might exceed the threshold, triggering an alert.

The way this is may be done is that the entire set of concepts corresponding to all the diseases in the disease template database will be examined. (Note that diseases will likely share many concepts, for instance, "high fever".) So if a large group of patients have concepts A, B, M, N, and Z, even though none of these correspond to any of the disease templates (and possibly to none of the known infectious diseases, such as, flu), this may suffice to generate an alert.

One of the key features of the present invention is to detect unusual patterns. For instance, disease patterns of known diseases may be used as filters to reduce false alerts. Additionally, seasonal information may be used to warn about unusual occurrences—for instance, many patients with flu-like symptoms in New York City, out of flu season. (Again we will be looking inside the patient record).

Another feature may be that if a large number of patients have flu-like symptoms, but also have another unusual symptom (not associated with the flu—for instance, hair loss) that may suffice to raise suspicion. Unusualness can be measured against known disease patterns. Also it can be measured against retrospective records—for instance, if there was no record of this combination of concepts (A, B, Q, R, M) in any patients in the last two years, that may suffice to raise a flag. (This would obviously require massive offline computation of past records—however, this can be simplified by extracting the entire set of concepts from all past patient records, and using that list to efficiently generate a quick match for unusualness).

In step 405, a determination is made as to whether the estimated probabilities of a disease incident exceeds corresponding threshold values. If the threshold is exceeded, in step 406, a disease outbreak alert will be outputted. The threshold value may vary depending on disease, terror threat level, and be adjusted to reduce false alerts.

In addition to a disease outbreak alert, a request for information may be output. This request for information may include a request to a physician to verify the existence of specified symptoms or to perform additional tests.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for automated identification of disease outbreak, the method comprising:
    obtaining patient records for patients being treated, at least some of the patient records containing information derived with a processor by data mining from individual data collections of the patients being treated, the information derived with the processor from an unstructured data source including text format, image information, waveform information or combinations thereof, the patient records being a machine readable structured dataset including the information derived with the processor from the unstructured data source and information from a structured data source;
    correlating selected patient data from the structured dataset, including data from the unstructured data source, contained in the patient records with disease indicia for at least one disease;
    identifying an anomaly at least in part based on the correlations;
    outputting an alert about the anomaly;
    extracting information from a plurality of clinical data sources to create a set of probabilistic assertions;
    combining the set of probabilistic assertions to create one or more unified probabilistic assertions; and
    inferring patient symptoms from the one or more unified probabilistic assertions.

2. The method of claim 1, wherein identifying the anomaly comprises estimating a probability of a disease outbreak:
    wherein outputting comprises outputting a disease outbreak alert, if any of the estimated probabilities exceeds a corresponding threshold value.

3. The method of claim 1, wherein the selected patient data includes information regarding patient symptoms in the patient record.

4. The method of claim 3, wherein the information regarding patient symptoms is derived at least in part from treatment notes.

5. The method of claim 1, wherein the disease indicia are specified by disease progression models stored in a disease knowledge base.

6. The method of claim 2, wherein the outputted disease outbreak alert includes information regarding suspect patients.

7. The method of claim 6, wherein the outputted information about the suspect patients preserves the anonymity of the suspect patients.

8. The method of claim 1, wherein the obtained patient records include information derived from a structured data source.

9. The method of claim 8, wherein the structured data source includes at least one database.

10. The method of claim 9, wherein the at least one database contains one or more of laboratory information, prescription information, test result information or combinations thereof.

11. The method of claim 1, wherein the unstructured data source stores information in text format.

12. The method of claim 11, wherein the information in text format includes one or more of treatment notes, admission slips, reports or combinations thereof.

13. The method of claim 1, wherein the disease indicia includes expected symptoms.

14. The method of claim 1, wherein at least some of the disease indicia are temporally defined.

15. The method of claim 1, wherein the selected patient data and the disease indicia for a disease partially match.

16. The method of claim 1, wherein the obtained patient records include information gathered from different hospital departments.

17. The method of claim 1, wherein the disease indicia includes observation of a cluster of patients having a partial match.

18. The method of claim 17, wherein the cluster is defined using geographic criteria.

19. The method of claim 1, wherein identifying the anomaly comprises estimating a probability of a disease outbreak, wherein the estimated probability is a joint probability that at least one patient has one of the diseases.

20. The method of claim 2, wherein the outputted disease outbreak alert includes a request for additional information.

21. The method of claim 20, wherein the request for additional information includes a request to verify the existence of a specified symptom.

22. The method of claim 20, wherein the request for additional information includes a request to perform a specified task.

23. The method of claim 2, wherein the threshold values vary depending on disease.

24. The method of claim 2, wherein the threshold values vary depending on terror threat level.

25. The method of claim 2, wherein the threshold values vary depending on previous false alerts.

26. The method of claim 1, wherein the correlating is performed at a central location and the data sources are provided using a networked hospital information system.

27. The method of claim 2, wherein the outputted disease outbreak alert is sent to a monitoring facility.

28. The method of claim 2, wherein the outputted disease outbreak alert is sent to a government agency.

29. The method of claim 2, wherein the disease outbreak alert is outputted when anomalous symptoms are found for a cluster.

30. The method of claim 29 where the anomalous symptoms are determined with respect to previous patients whose records are available.

31. The method of claim 2, wherein the disease outbreak alert is outputted even though patient disease progressions do not follow expected disease progressions.

32. The method of claim 31, wherein the disease indicia are extracted from a set of previous patients to facilitate detection of anomalous patterns.

33. The method of claim 32, wherein the disease outbreak alert is outputted when more than a predetermined number of patients in a geographic cluster are found to have anomalous symptoms.

34. A program storage device readable by a machine, the program storage device tangibly embodying a program of instructions executable on the machine to perform a method for automated identification of disease outbreak, the method comprising:
    obtaining patient records for patients being treated, at least some of the patient records containing information derived with a processor by data mining from individual data collections of the patients being treated, the information derived with the processor from an unstructured data source including text format, image information, waveform information or combinations thereof, the patient records being a machine readable structured dataset including the information derived with the processor from the unstructured data source and information from a structured data source;
    correlating selected patient data from the structured dataset, including data from the unstructured data source, contained in the patient records with disease indicia for at least one disease;
    identifying an anomaly at least in part based on the correlations;
    outputting an alert about the anomaly;
    extracting information from a plurality of clinical data sources to create a set of probabilistic assertions;
    combining the set of probabilistic assertions to create one or more unified probabilistic assertions; and
    inferring patient symptoms from the one or more unified probabilistic assertions.

35. The program storage device of claim 34 wherein the instructions for identifying the anomaly comprise estimating a probability of a disease outbreak.

36. The method of claim 1 wherein identifying the anomaly comprises identifying a particular patient.

37. A method for automated identification of disease outbreak, the method comprising:
    data mining for selected patient data as a function of a knowledge base;
    inferring symptoms from the mined data as a function of probabilities in the knowledge base;
    correlating the selected patient data contained in patient records with disease indicia for at least one disease;
    estimating a probability of disease outbreak at least in part based on the correlations;
    indicating a disease outbreak if the estimated probability exceed a threshold value; and
    outputting a disease outbreak alert for the disease outbreak,
    extracting information from a plurality of clinical data sources to create a set of probabilistic assertions;
    combining the set of probabilistic assertions to create one or more unified probabilistic assertions; and
    inferring patient symptoms from the one or more unified probabilistic assertions.

38. The method of claim 37 wherein the selected patient data includes information regarding patient symptoms.

39. The method of claim 37 wherein the mining comprises:
    extracting information from a plurality of clinical data sources to create a set of probabilistic assertions; and
    wherein the inferring comprises combining the set of probabilistic assertions to create one or more unified probabilistic assertion; and inferring patient symptoms from the one or more unified probabilistic assertion.

40. The method of claim 37 wherein the selected patient data and the disease indicia for a disease partially match.

41. The method of claim 37 wherein the disease indicia includes observation of a cluster of patients having a partial match.

42. The method of claim 37 wherein the estimated probability is a joint probability that at least one patient has one of the diseases.

43. The method of claim 37 wherein the threshold values vary depending on disease.

44. The method of claim 37 wherein the threshold values vary depending on terror threat level.

45. A method for automated identification of disease outbreak, the method comprising:
  obtaining with a machine selected patient data record in patient records, the selected patient data including evidence of one or more symptoms in the patient record, the symptoms inferred from the patient data with probabilities in a knowledge base;
  identifying with the machine an unusual concentration of the symptoms from the selected patient data;
  outputting an regarding the unusual concentration;
  wherein obtaining comprises extracting information from a plurality of clinical data sources to create a set of probabilistic assertions;
  combining the set of probabilistic assertions to create one or more unified probabilistic assertions; and
  inferring patient symptoms from the one or more unified probabilistic assertions.

46. The method of claim 45 further comprising estimating a probability of disease outbreak as a function of the unusual concentration.

47. The method of claim 45 wherein obtaining comprises obtaining from unstructured patient records.

48. The method of claim 45 wherein identifying comprises identifying the unusual concentration geographically.

49. The method of claim 45 wherein identifying comprises correlating the selected patient data with disease indicia for at least one disease.

50. The method of claim 1 wherein the indicia are provided by the Centers for Disease Control and Prevention or another government agency.

51. The method of claim 37 wherein the indicia are provided by the Centers for Disease Control and Prevention or another government agency.

52. The method of claim 1 wherein the patient records are obtained from health care facilities or hospitals.

53. The method of claim 37 wherein the selected patient data is obtained from health care facilities or hospitals.

* * * * *